United States Patent [19]

Birum

[11] 4,036,913
[45] July 19, 1977

[54] PHOSPHORUS COMPOUNDS

[75] Inventor: Gail H. Birum, Kirkwood, Mo.

[73] Assignee: Monsanto Company, St. Louis, Mo.

[21] Appl. No.: 595,959

[22] Filed: July 14, 1975

Related U.S. Application Data

[63] Continuation-in-part of Ser. No. 385,779, Aug. 6, 1973, Pat. No. 3,954,860.

[51] Int. Cl.$^2$ .............................. C07F 9/32; C07F 9/40; C07F 9/53
[52] U.S. Cl. .................................................. 260/938
[58] Field of Search ......................................... 260/938

[56] References Cited

U.S. PATENT DOCUMENTS 3,660,413   5/1972   Cates ........................... 260/938 X

*Primary Examiner*—Anton H. Sutto
*Attorney, Agent, or Firm*—Herman O. Bauermeister

[57] ABSTRACT

The present invention relates to new nitrogen-containing organophosphorus compounds having aryloxy substituents bonded to phosphorus in ester structures.

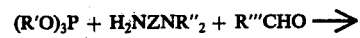

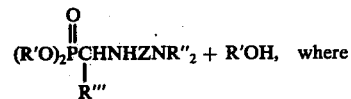

where

R' is aryl of 6 to 10 carbon atoms,
R" is hydrogen, alkyl, aryl or haloaryl of 1 to 15 carbon atoms, or no more than one carboethoxymethyl group, and where the halogen on the aryl group is bromine, chlorine or fluorine,
R''' is alkyl, alkenyl or aryl groups of 1 to 15 carbon atoms and substituted aryl forms where the subtituent is fluorine, chlorine, bromine, nitro, cyano, hydroxyl, alkyloxy or mixtures of such substituents, and
Z is CO, CS or SO$_2$.

The phosphorus compounds have utility as fire retardants and as biologically active materials.

7 Claims, No Drawings

PHOSPHORUS COMPOUNDS

The present patent application is a continuation-in-part of Ser. No. 385,779, filed Aug. 6, 1973, now U.S. Pat. No. 3,954,860.

The present invention relates to new nitrogen-containing organophosphorus compounds having aryloxy substituents bonded to phosphorus in ester structures. They can be hydrolyzed to the corresponding acids.

A new process for the production of such compounds is also a part of the present invention.

The general method for the production of the novel nitrogen-containing organophosphorus compositions is in accordance with the equation shown below:

$$(R'O)_3P + H_2NZNR''_2 + R'''CHO \longrightarrow$$

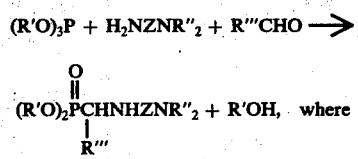

R' is aryl of 6 to 10 carbon atoms,
R" is hydrogen, alkyl, aryl or haloaryl of 1 to 15 carbon atoms, or no more than one carboethoxymethyl group, and where the halogen on the aryl group is bromine, chlorine, or fluorine,
R''' is alkyl, alkenyl or aryl of 1 to 15 carbon atoms and substituted aryl forms where the substituent is fluorine, chlorine, bromine, nitro, cyano, hydroxyl, alkyloxy or mixtures of such substituents, and
Z is CO, CS or $SO_2$.

A specific compound is:

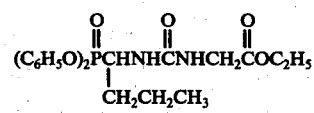

When both R" radicals of the reactant, $H_2NZNR''_2$, are hydrogen, the product can also contain two phosphorus moieties according to the formula

exemplified by

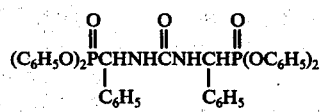

For the production of the desired monophosphonate esters of the present invention, as the major product, it is preferred to employ the reactants $(R'O)_3P$ and $R'''CHO$, each in substantially less than two molar proportions relative to the third reactant, $H_2NZNH_2$. A minor proportion of the diphosphonate ester is also obtained. However, if at least two molar proportions of both $(R'O)_3P$ and $R'''CHO$ are used relative to $H_2NZNH_2$, and the temperature and time employed are sufficient to complete the reaction, the diphosphorus-containing product may be obtained essentially exclusively.

Formation of the compounds of this invention is usually initiated when a mixture of the three reactants, preferably in an inert solvent such as toluene and chlorobenzene, is warmed to about 70° C. The reaction is usually complete after one hour at 80°–120° C., but warming at higher or lower temperatures is sometimes advantageous. An alternate procedure, which may facilitate control of heat of reaction, is to gradually add the aldehyde reactant to a stirred mixture of the phosphorus ester and urea reactants in a solvent at reaction temperature, generally from about 70° C to 120° C.

When R' is an unsubstituted alkyl radical, the reaction is generally slow unless acid catalysts are used, particularly boron trifluoride etherate or carboxylic acids, such as acetic acid, propionic acid, butyric acid and benzoic acid.

Preferably, R' is an aryl radical since phosphorus ester reactants containing these radicals are relatively reactive in the present invention and usually give good yields of products without the necessity for use of catalysts or long reaction times such as is frequently the case when R' is an alkyl radical. This is surprising since alkyl esters of trivalent phosphorus acids are normally much more reactive than aryl esters in other types of reactions.

The ester products of the present invention may be hydrolyzed to the corresponding acids. Thus, when one R' is hydrocarbyloxy, the ester may be hydrolyzed to the corresponding phosphinic acid.

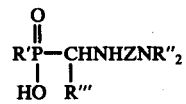

If both radicals are hydrocarbyloxy, the esters are hydrolyzed to phosphinic acids.

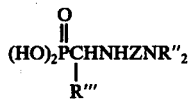

exemplified by

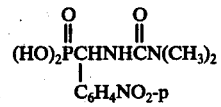

Specific examples showing the preparation of representative compounds of the present invention are set forth herewith, but are not limitative of the scope of the invention.

EXAMPLE 1

Tetraphenyl (ureylenediethyl)diphosphonate

A mixture of 60.0g (1.0 mole) of powdered urea, 620.5g (2.0 moles) of freshly distilled triphenyl phosphite, and 88.0g (2.0 moles) of freshly distilled acetaldehyde in 600g of 1,2-dichloroethane is stirred under nitrogen and warmed to 60° C to initiate reaction. Cooling is used for a few minutes to keep the temperature below 80°, and the reaction mixture is then warmed at 80°-84° for 0.5 hr to give a light tan solution having $^{31}$P nmr signals at −19.7 ppm(m) and at −16.1 ppm (trace). The solution is washed three times with 10% sodium carbonate solution and three times with water, and it is then stripped to 130°/0.3mm to give 508.5g (87.6%) of yellow, viscous oil having a $^{31}$P nmr signal only at −19.9 ppm. A solution of 158g of this oil in acetonitrile is refrigerated for three days to induce crystallization. It is then filtered, and the solid washed with acetonitrile, giving 112.3g (62%) of white solid, mp ~125°-155°. Repeated recrystallizations from acetonitrile gives fractions I and II. Fraction I: mp 136°-138°; $^{31}$P nmr (CDCl$_3$) −19.7(m, J ~18Hz); $^1$H nmr δ7.21(m, 20, C$_6$H$_5$), 6.46 (d, 2, J = 12Hz, NH; collapsing to a singlet upon homonuclear decoupling), 4.86 (m, 2, CH), 1.30 (d of d, 6, J = 18 and 7.5Hz, CH$_3$; collapsing to a doublet, J = 7.5Hz, upon irradiation with 40.5 MHz at 750Hz and to a doublet, J = 18 Hz, upon homonuclear decoupling); ir(KBr) 2.99μ(m), 3.27(w), 5.92(s), 6.26(m), 6.43(s), 6.68(s), 8.40(vs), 10.6(vs); molecular weight (CHCl$_3$) 572 (theory 580).

Anal. Calcd for C$_{29}$H$_{30}$N$_2$O$_7$P$_2$: C, 59.98; H, 5.21; N, 4.82; P, 10.67. Found: C, 60.08; H, 5.05; N, 4.67; P, 10.71.

Fraction II: mp 156°-161°; δ$^{31}$P −20.5 (m, J≈17.8Hz); $^1$H nmr δ7.20 (m, 20), 6.55 (d, 2, J = 10, NH), 4.86 (m, 2, CH), 1.37 (d of d, 6, J = 18 and 7.5Hz, CH$_3$); ir essentially identical to I.

When the reaction is repeated without the use of a solvent, the results are essentially the same according to nmr measurements. In this run the by-product phenol (81% of theory) is removed by stripping to 120°/1mm.

EXAMPLE 2

Tetraphenyl (ureylenedibenzyl)diphosphonate

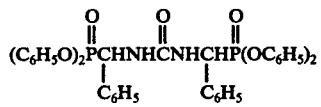

A mixture of 60.0g (1.0 mole) of powdered urea, 620.5g (2.0 moles) of freshly distilled triphenyl phosphite, and 212.2g (2.0 moles) of benzaldehyde in 600g of 1,2-dichloroethane is stirred under nitrogen and warmed. The heating mantle is removed at 70°, and a cooling bath is used as needed for 0.3 hr to keep the temperature below 83°. The reaction mixture is warmed at reflux (93°) for 0.7 hr and then allowed to cool. One pint of CCl$_4$ is added and the solution is washed once with one liter of 10% NaOH solution, three times with 500 ml of 5% NaOH solution, and three times with 500 ml of water. Stripping to 115°/0.2mm gives 498g (71%) of pale yellow viscous oil; $^{31}$P nmr −15ppm (overlapping doublets). Two fractions, I and II, are separated by repeated recrystallizations from acetone and acetonitrile. Fraction I: white solid, mp 189°-191°; $^{31}$P nmr (CDCl$_3$) −14.7 ppm (d, J = 22Hz); $^1$H nmr δ6.66 to 7.66 (m, 32, aryl and NH), 5.98 (d of d, 2, J = 22 and 10Hz, CH; collapsing to doublet, J = 10Hz, when decoupled from phosphorus); ir (KBr) 2.98(m), 3.27(w), 5.88(s), 6.27(m), 6.43(s), 6.67(s), 8.38(vs), 10.6(vs); molecular weight (acetone) 731 (theory 704).

Anal. Calcd for C$_{39}$H$_{34}$N$_2$O$_7$P$_2$: C, 66.47; H, 4.86; N, 3.98; P, 8.79. Found: C, 66.35; H, 4.82; N, 3.99; P, 9.08.

Fraction II: white solid, mp 181°-183°; $^{31}$P nmr −15.5 ppm (d, J = 22Hz); $^1$H nmr δ6.66 to 7.75 (m, 32, aryl and NH), 6.06 (d of d, 2, J = 22 and 10Hz, CH; collapsing to doublet, J = 10Hz, when decoupled from phosphorus); ir (KBr) essentially the same as I; molecular weight (acetone) 692 (theory 704).

Anal. Found: C, 66.45; H, 4.83; N, 3.93; P, 8.71. The mixed mp of I and II was 159°-173°.

EXAMPLE 3

Tetra(p-tolyl) (ureylenedibenzyl)diphosphonate

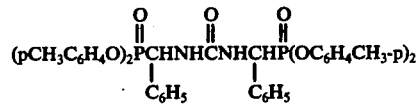

Benzaldehyde, 53.1g (0.5 mole), is added dropwise to a stirred mixture of 15.0g (0.25 mole) of urea, 176.2g (0.5 mole) of tris-(p-tolyl) phosphite, and 150g of benzene at 60°-80°. The mixture is then warmed at 90° for 2.5 hr, giving a light yellow solution having overlapping $^{31}$P nmr doublets centered at −14.7 ppm. The reaction mixture is stripped to 125°/0.5mm, and a portion of the glassy residue is recrystallized twice from acetonitrile to give a white solid that appears to be a single isomer: mp 189°-191°, $^{31}$P nmr −15.1 ppm (d, J = 22Hz); $^1$H nmr δ6.5-7.6(m, 28, aryl and NH), 5.8 (d of d, 2, J = 22 and 10Hz, PCHNH), 2.2(s, 12, CH$_3$).

Anal. Calcd for C$_{43}$H$_{42}$N$_2$O$_7$P$_2$: C, 67.89; H, 5.56; N, 3.68; P, 8.14. Found: C, 67.98; H, 5.52; N, 3.60; P, 8.23.

EXAMPLE 4

Tetraphenyl 1,1'-(sulfonyldiamino)bis(ethylphosphonate)

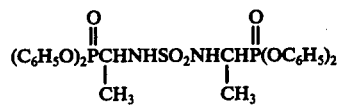

About one-fourth of 0.52 mole of acetaldehyde is added to a stirred mixture of 0.50 mole of triphenyl phosphite and 0.25 mole of sulfamide in 200g of chlorobenzene. When this mixture is warmed to about 70° reaction is initiated, and the remainder of the acetaldehyde is added dropwise at 70°-80° with cooling until heat of reaction subsides. The reaction mixture is warmed at 80°-95° C for one hr, and the chlorobenzene solvent is stripped at reduced pressure. The addition of 200 ml of ether to the residue and then cooling in ice water causes a solid to separate. This is recrystallized from acetonitrile to give a white solid product: mp 192°-194° C; $^{31}$P nmr(DMSO-d$_6$) −18.6(m, J~18Hz).

Anal. Calcd for C$_{28}$H$_{30}$N$_2$O$_8$P$_2$S: C, 54.54; H, 4.90; N, 4.54; P, 10.05; S, 5.20. Found: C, 54.19; H, 4.81; N, 4.28; P, 9.90; S, 5.17.

EXAMPLE 5

Tetraphenyl (thiourylenedibutyl)diphosphonate

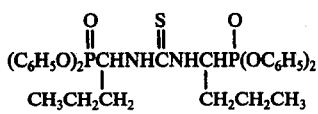

When a mixture of 11.4g (0.15 mole) of thiourea, 93.0g (0.30 mole) of triphenyl phosphite, and 22.7g (0.32 mole) of n-butyraldehyde in 75g of toluene is warmed to 100° C, reaction is initiated, and the temperature increases to 105° within a few minutes without external warming. The reaction mixture is then warmed at 105°–110° for 1 hr to give a light yellow solution having a $^{31}P$ nmr peak at $-18.0$ ppm, the only observable signal. Concentration to 120°/0.5mm to remove solvent and most of the by-product phenol gives 103.5g (theory 97.5g) of viscous liquid that completely solidifies on standing. Recrystallization of a portion twice from acetone and once from acetonitrile gives a white solid (2): mp 138°–143°; $^{31}P$ nmr − 18.1 ppm; $^1H$ nmr δ7.3 (d, 2, J = 10Hz, NH), 7.1 (m, 20, aryl), 5.8 (m, 2, CH), 0.3–2.1 (m, 14, C$\underline{H_2CH_2CH_3}$); ir 3.04(w), 3.26(w), 3.40(w), 6.28(m), 6.45(m), 6.70(m), 7.36(m), 7.93(m), 8.29(m), 8.43(s), 10.6–10.7(vs), 13.0(vs), 14.5(s); molecular weight (acetone) 630 (calcd 652).

Anal. Calcd for $C_{33}H_{38}N_2O_6P_2S$: C, 60.72; H, 5.87; N, 4.29; P, 9.49; S, 4.91. Found: C, 60.87; H, 6.09; N, 4.55; P, 9.56; S, 5.08.

EXAMPLE 6

Diphenyl[4-nitro-α-(ureido)benzyl]phosphonate

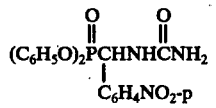

A mixture of 21.0g (0.139 mole) of 4-nitrobenzaldehyde, 43.2g (0.139 mole) of triphenyl phosphite, and 8.3g (0.139 mole) of powdered urea in 50g of 1,2-dichloroethane is warmed to 80° and the mantle is removed. After heat of reaction subsides, the reaction mixture is warmed at 80°–90° C for 0.5 hr giving a yellow solution: $^{31}P$ nmr ∼ −15 ppm (d, J = 23Hz, major signal), −16.6 (trace), +14.1 (trace). The reaction mixture is diluted with cyclohexane and allowed to stand. After four weeks a solid is separated by decantation. It is recrystallized three times from acetonitrile to give 5.5g of white solid: mp 169°–175°; $^{31}P$ nmr (DMSO) −14.8 ppm (d, J = 23Hz); ir (KBr) 2.93(m), 6.00(s), 6.28(s), 6.55(s), 6.69(s), 7.40(s), 8.28(s), 8.47(s); molecular weight (acetone) 423 (calcd 427).

Anal. Calcd for $C_{20}H_{18}N_3O_6P$: C, 56.19; H, 4.24; N, 9.83; P, 7.25.
Found: C, 56.48; H, 4.22; N, 9.97; P, 6.91.

EXAMPLE 7

Diphenyl(1-ureidobutyl)phosphine oxide

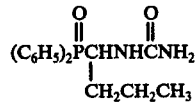

When a mixture of 0.50 mole of ethyl diphenylphosphinite 0.55 mole of n-butyraldehyde, and 0.25 mole of urea in 150 ml of chlorobenzene is warmed at 110° C for 3 hr, there is only a slow reaction. The mixture is cooled to room temperature and 0.25 mole of acetic acid is added dropwise in ∼10 minutes. The temperature increases to 65° during this addition; the urea dissolves and then a white solid product separates. The addition of another 0.25 mole of acetic acid causes no additional heat of reaction. The reaction mixture is warmed at 65°–80° for 9.5 hr and filtered, giving 44.4g. Recrystallization from ethylene glycol gives 26.5g of a white solid: mp 241°–244°; $^{31}P$ nmr (CF$_3$CO$_2$H) −44.4 ppm; ms M$^+$ = 316 (theory 316).

Anal. Calcd for $C_{17}H_{21}N_2O_2P$: N, 8.85; P, 9.79. Found: N, 8.62; P, 9.94.

EXAMPLE 8

Diphenyl [1-(3-phenylureido)ethyl]phosphonate

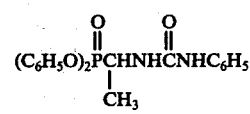

When 17.6g (0.4 mole) of acetaldehyde is added to a stirred mixture of 54.4g (0.4 mole) of phenylurea and 124.0g (0.4 mole) of triphenyl phosphite in 200g of 1,2-dichloroethane, heat of reaction raises the temperature to 47° C. The reaction mixture is then warmed to 90° to give a light brown solution having $^{31}P$ nmr at −127.5 ppm for unreacted phosphite and at −20.4 ppm(m) (∼1:4 area ratio). The solution is cooled to room temperature and washed with 400 ml of 10% NaOH solution, with 400ml of 5% NaOH solution and twice with 400 ml of water and then stripped to 55°/10mm. The warm residue is diluted with acetone, and the solution is cooled and filtered giving 57g of white solid having a $^{31}P$ nmr multiplet at −20.9 ppm. This is recrystallized twice from acetone to give a white solid: mp 132°–133.5°; $^{31}P$ nmr −20.7 ppm (m, J ∼18.2Hz); ir (KBr) 3.03(s), 5.88(s), 6.25(s), 6.40(s), 6.64(s), 7.53(s), 8.2–8.3(vs), 10.5–10.7(vs); molecular weight (acetone) 403 (calcd 396).

Anal. Calcd for $C_{21}H_{23}N_2O_4P$: C, 63.61; H, 5.34; N, 7.07; P, 7.81. Found: C, 63.82; H, 5.40; N, 6.96; P, 7.81.

EXAMPLE 9

Ethyl [3-(1-diphenoxyphosphinylbutyl)ureido] acetate

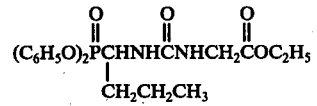

When a mixture of 43.8g (0.3 mole) of ethyl hydantoate, 93.0g (0.3 mole) of triphenyl phosphite, and 21.6g (0.3 mole) of n-butylaldehyde in 100g of benzene is warmed to 65° C, heat of reaction becomes sufficient to raise the temperature to 82° (reflux) without external warming. Warming at reflux is continued for 0.5 hr giving a clear, colorless solution having a single $^{31}P$ nmr peak, −19.2 ppm. The solvent and most of the phenol are removed by stripping to 117°/1mm. The crude product is diluted with an equal volume of ether, and this solution is cooled to 10° and filtered to give 87.6g (68%) of white solid: mp 114°–116° (from CH$_3$CN); $^{31}P$ nmr −19.7 ppm; $^1$H nmr δ7.1 (m, 10, aryl), 6.5 (d, 1, J = 10Hz, CHN$\underline{H}$), 6.1 (broad, 1, N$\underline{H}$CH$_2$,), 4.8 (m, 1, C$\underline{H}$), 4.1 (q, 2, J = 7Hz, OC$\underline{H}_2$CH$_3$), 3.8 (broad, 2, NHC$\underline{H}_2$), 1.2 (t, 3, J = 7Hz, 0CH$_2$C$\underline{H}_3$), 0.8–1.5 (m, 7, C$\underline{H}_2$C$\underline{H}_2$CH$_3$).

Anal. Calcd for C$_{21}$H$_{27}$N$_2$O$_6$P: C, 58.04; H, 6.26; N, 6.45; P, 7.13. Found: C, 57.82; H, 6.19; N, 6.24; P, 6.89.

EXAMPLE 10

Diphenyl [4-fluoro-α-(3-phenylureido)benzyl] phosphonate

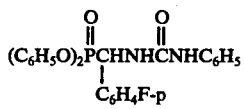

A mixture of 27.2g (0.2 mole) of phenylurea, 25.0g (0.2 mole) of 4-fluorobenzaldehyde, and 62.0g (0.2 mole) of triphenyl phosphite in 150g of benzene is warmed at reflux for 1.5 hr to give a brown solution from which a white solid (41.6g) separates upon cooling. Recrystallization from acetonitrilebenzene gives 30g; mp 201°–207° C; $^{31}$P nmr −16.2 ppm (d, J = 24Hz).

EXAMPLE 11

Diphenyl α-[3-(4-chlorophenyl)ureido]-4-hydroxy-3-methoxybenzyl phosphonate

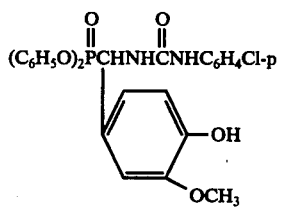

A mixture of 34.1g (0.2 mole) of 4-chlorophenylurea, 62.1g (0.2 mole) of triphenyl phosphite, and 30.4g (0.2 mole) of vanillin in 150 ml of benzene is warmed at reflux for 2.5 hr. The reaction mixture is cooled and filtered to give a light yellow solid which is twice recrystallized from acetonitrile-ethylene dichloride: mp 190°–194° dec; $^{31}$P nmr − 15.8 ppm (d, J = 22Hz); $^1$H nmr δ9.1 (s, 1, N$\underline{H}$C$_6$H$_4$Cl), 8.7 (s, 1, OH), 6.7–7.8 (m, 18, aryl and CHN$\underline{H}$), 5.7 (d of d, 1, J = 22 and 10 Hz, PC$\underline{H}$NH), 3.8 (s, 3, CH$_3$).

Anal. Calcd for C$_{27}$H$_{24}$ClN$_2$O$_6$P: C, 60.17; H, 4.48; Cl, 6.58; N, 5.19; P, 5.75. Found: C, 59.62; H, 4.36; Cl, 6.50; N, 5.13; P, 5.65.

EXAMPLE 12

Diphenyl{1-[3-(4-chlorophenyl)ureido]butyl}phosphine oxide

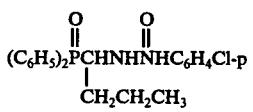

A mixture of 0.15 mole each of p-chlorophenylurea, phenyl diphenylphosphinite, and n-butylraldehyde in 150g of toluene is warmed at reflux for 5.5 hr, giving a reaction mixture having a $^{31}$P nmr signal only at −36.8 ppm. When the toluene is removed at reduced pressure, the residue solidifies. Recrystallization of a portion from benzene gives a white solid: mp 275°–278° C; $^{31}$P nmr −37.4 ppm; $^1$H nmr δ9.1 (s, 1, N$\underline{H}$C$_6$H$_4$Cl), 6.4–8.1 (m, 15, aryl and CHN$\underline{H}$), 5.1 (m, 1, PCH), 0.6–2.0 (m, 7, CH$_2$CH$_2$CH$_3$).

Anal. Calcd for C$_{23}$H$_{24}$ClN$_2$O$_2$P: C, 64.70; H, 5.67; N, 6.56; Cl, 8.30; P, 7.25. Found: C, 65.45; H, 5.62; N, 6.55; Cl, 8.59; P, 7.20.

EXAMPLE 13

Diphenyl α-(3,3-diphenylureido)-4-nitrobenzylphosphonate.

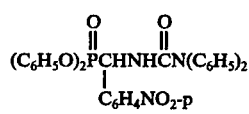

A mixture of 21.2g (0.1 mole) of 1,1-diphenylurea, 15.1g (0.1 mole) of 4-nitrobenzaldehyde, and 31.0g (0.1 mole) of triphenyl phosphite in 50g of benzene is stirred under nitrogen and warmed at reflux (87° C) for 2 hours to give a light yellow solution: $^{31}$P nmr −13.2 (d, J = 23Hz), −127.8 ppm (area ratio 5:1). Most of the benzene is removed at reduced pressure, and ether is stirred into the yellow oil remaining, causing 32g of solid to separate after a few minutes. A portion is recrystallized from acetonitrile to give a white solid: mp 157°–162°; $^{31}$P nmr −13.2 ppm (d, J = 24Hz); molecular weight (CHCl$_3$) 565 (calcd 579).

Anal. Calcd: C, 66.30; H, 4.52; N, 7.25; P, 5.34. Found: C, 66.41; H, 4.55; N, 7.23; P, 5.24.

EXAMPLE 14

1-(3,3-Diphenylureido)ethylphosphonic acid.

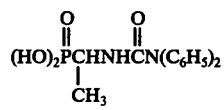

Freshly distilled acetaldehyde (0.22 mole) is added during 0.5 hr to a stirred solution of 0.1 mole each of 1,1-diphenylurea and triphenyl phosphite in 130g of benzene at 60° C. The solution is warmed at reflux (65°–70° with Dry Ice-cooled condenser) for 1.25 hr, giving a dark brown solution having a small $^{31}$P nmr peak at −126.2 ppm for unreacted phosphite and a large product peak at −18.4 ppm (~1:5 areas). The reaction mixture is stripped to 130°/3mm. The residue is diluted with 200 ml of acetonitrile and 10 g of H$_2$O, and this solution is warmed at reflux for 3 hr. Solid that separates during warming is recrystallized from acetic acid-water to give a white solid; mp 186°–187° C dec; P$^{31}$ nmr −21.6 ppm; $^1$H nmr δ10.0 (s, 2, OH), 7.3 (m, 10, C$_6$H$_5$), 5.4 (d of d, 1, J = 9 and 5Hz, NR), 4.1 (m, 1, CH), 1.3 (d of d, 3, J = 16 and 7 Hz, CH$_3$); acidity 2.00 equiv/mole, pK$_1$ = 2.20, pK$_2$ = 8.62.

Anal. Calcd for C$_{15}$H$_{17}$N$_2$O$_4$P: C, 56.25; H, 5.35; N, 8.75; P, 9.67. Found: C, 56.43; H, 5.36; N, 8.84; P, 9.60.

EXAMPLE 15

[α-(3,3-Dimethylureido)-4-nitrobenzyl]phosphonic acid.

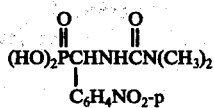

A mixture of 30.2g (0.2 mole) of 4-nitrobenzaldehyde, 17.6g (0.2 mole) of 1,1-dimethylurea and 62.0g (0.2 mole) of triphenyl phosphite in 100 ml of benzene is warmed at 86°–87° for 1.5 hr to give a clear yellow solution: $^{31}$P nmr −13.4 pm (d, J = 23 Hz) and −127.9 ppm (area ratio ~5:1). The reaction mixture is stirred as it cools, and it is then filtered to give 54.1g of off-white solid (mp 155°–170° after recrystallization from acetonitrile). A solution of this solid in acetone-water (10:1) is refluxed for 2 hours and then allowed to stand open to the atmosphere for 10 days. Acetonitrile is added to the residue, and the mixture is warmed to boiling and then filtered while hot to give a yellow solid. Recrystallization once from acetonitrile-ethanol and twice from isopropanol gives white solid: mp 187°–205° (dec.); $^{31}$P nmr (CD$_3$SOCD$_3$) −16.4 ppm (d, J = 24Hz); $^1$H nmr δ11.1 (s, 2, OH), 8.1 (d of d, 4, aryl), 6.5 (m, 1, NH), 5.3 (d of d, 1, J = 24 and 8Hz, CH), 2.9 (s, 6, CH$_3$). Anal. Calcd for C$_{10}$H$_{14}$N$_3$O$_6$P: C, 39.60; H, 4.65; N, 13.86; P, 10.21. Found: C, 39.68; H, 4.75; N, 14.07; P, 10.38.

EXAMPLE 16

Diphenyl α-dimethylaminosulfonylaminobenzylphosphonate.

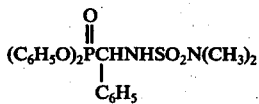

A mixture of 0.25 mole each of triphenyl phosphite, benzaldehyde, and N,N-dimethylsulfamide in 130g of chlorobenzene is warmed at 115° C. for 1.5 hrs. After the reaction mixture cools to room temperature, 41.0g (36% yield) of crude product is isolated by filtration. It is washed with water and recrystallized from chlorobenzene, giving a white solid: mp 193°–196°; $^{31}$P nmr (DMSO-d$_6$) −14.0 ppm(d, J = 28Hz); $^1$H nmr δ8.8(d of d, 1, J = 2 and 11, NH), 6.8–7.8(m, 15, aryl), 5.2(d of d, 1, J = 10 and 25Hz, CH), 2.4(s, 6, CH$_3$).

When p-chlorobenzaldehyde is similarly treated with triphenyl phosphite and N,N-dimethylsulfamide, the product is diphenyl δ-dimethylaminosulfonylamino-p-chlorobenzylphosphonate.

Tetraphenyl (ureylenedi-4-bromobenzyl)diphosphonate is obtained when a mixture of one mole of urea and two moles each of 4-bromobenzaldehyde and triphenyl phosphite in chlorobenzene is warmed at about 100° C.

EXAMPLE 17

Diphenyl 1-(dimethylaminosulfonylamino)butylphosphonate.

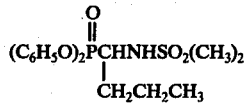

When a mixture of 0.3 mole each of triphenyl phosphite, n-butyraldehyde, and N,N-dimethylsulfamide in 150g of chlorobenzene is warmed to about 80° C., heat of reaction is observed and the temperature increases to 86° in 10 minutes. The reaction mixture is kept at 85°–90° for 1 hr more, and then it is stripped to 110°/2mm. Ether (150ml) is stirred into the cooled residue, causing 72.4g (59% yield) of solid product to form. Recrystallization of a portion from benzene gives a white solid: mp 114°–117°; $^{31}$P nmr (DMSO-d$_6$) −18.4 ppm.

When N,N-dimethylthiourea is similarly treated with triphenyl phosphite and methacrolein, the product is diphenyl 1-(3,3-dimethylthioureido)-2-methyl-2-propenylphosphonate.

EXAMPLE 18

Phenyl[1-(piperidinosulfonylamino)ethyl]phenylphosphinate.

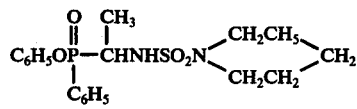

This compound is obtained in 75% yield in a crude form from a mixture of equimolar quantities of diphenyl phenylphosphonite, acetaldehyde, and piperidinosulfonylamine in chlorobenzene. Recrystallization of a portion twice from acetonitrile gives a white solid product: mp 152°–165°; $^{31}$P nmr(DMSO-d$_6$) −38.4 ppm.

EXAMPLE 19

Diphenyl 1-morpholinosulfonylamino)ethylphosphonate.

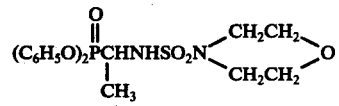

A mixture of 0.15 mole each of triphenyl phosphite, acetaldehyde, and morpholinosulfonylamine in 100g of chlorobenzene is warmed at 100° C. for 1.25 hrs, and the reaction mixture is stripped to 110°/0.15mm. The cooled residue is diluted with 100ml of ether, causing separation of 34.5g of crude solid product. Recrystallization of a portion from isopropyl alcohol gives a white solid, mp 104.5–108°, $^{31}$P nmr(DMSO-d$_6$) −18.1 ppm.

EXAMPLE 20

Diphenyl[1-(morpholinosulfonylamino)ethyl]phosphine oxide

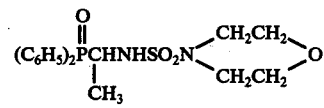

When a mixture of equimolar quantities of phenyl diphenylphosphinite, acetaldehyde, and morpholinosulfonylamine in chlorobenzene is treated by the procedure used in the preceding experiment, the product is a white solid, mp 215°–217° C., $^{31}$P nmr (DMSO-d$_6$) −30.9 ppm.

EXAMPLE 21

Diphenyl α-aminosulfonylaminobenzylphosphonate

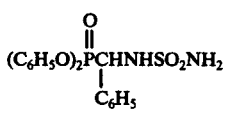

A mixture of equimolar quantities of triphenyl phosphite, benzaldehyde, and sulfamide in chlorobenzene is warmed at 95°–100° C. for 2.5 hrs, and then the reaction mixture is stripped to 120°/0.2mm. The residue is recrystallized from acetonitrile and then from chlorobenzene, giving a white solid: mp 171°–174°; $^{31}$P nmr(DMSO-d$_6$) −14.4(d, $J = $ 25Hz); $^1$H nmr δ8.2(d of d, 1, $J = $ 2 and 10Hz, NH), 6.9–7.6(m, 15, aryl), 6.7 (s, 2, NH$_2$), 5.2(d of d, 1, $J = $ 10 and 26, CH).

The filtrate remaining after recrystallization of the above product contains a minor amount of the diphosphonate ester.

EXAMPLE 22

Pre-emergent herbicidal activity of representative compounds of this invention is determined by the following procedure:

A good grade of top soil is placed in aluminum pans and compacted to a depth of ⅛ to ¼ inch from the top of the pan. A pre-determined number of seeds of each of several plant species are placed on top of the soil in the pans. The seeds are covered with soil and the pans leveled. The herbicidal composition is applied by spraying the surface of the top layer of soil with a solution containing a sufficient amount of active ingredient to obtain a rate of application of 10 lbs. per acre. The pans are then placed on a sand bench in the greenhouse and watered from below as needed. The plants are observed at the end of approximately 14 days and the results recorded.

Pre-emergent activity of the compounds prepared in the designated Examples is observed against the species as shown in the table below, wherein Y denotes that herbicidal activity is observed.

In general, compounds of the formula

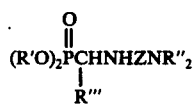

are useful in this relationship.

| PRE-EMERGENT TESTING | |
|---|---|
| Compound of Example | 13 |
| General Narrowleaf | X |
| General Broadleaf | X |

-continued

| PRE-EMERGENT TESTING | |
|---|---|
| Compound of Example | 13 |
| Canada Thistle | X |
| Cocklebur | |
| Velvetleaf | |
| Morning Glory | |
| Lambsquarters | X |
| Smartweed | X |
| Nutsedge | |
| Quackgrass | |
| Johnsongrass | X |
| Downy Brome | X |
| Barnyardgrass | |

Compounds of this invention are also useful as synergists in enhancing the fire-retardance of halogen-containing polymers. For example, the fire retardant property of polyvinyl chloride is improved by use of materials of this invention, which provide the advantage of introducing phosphorus, for example, in the proportion of about 1% to 10% by weight relative to the polyvinyl chloride. Compounds useful for this purpose include the products of Examples 6, 8, 9, 10, 13, 16, 17, 19 and 21.

In general, compounds of the formula

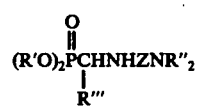

are useful in this relationship.

What is claimed is:

1.

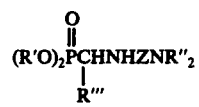

where
R' is aryl of 6 to 10 carbon atoms,
R'' is hydrogen, alkyl, aryl or haloaryl of 1 to 15 carbon atoms, or no more than one carboalkyloxymethyl group, and where the halogen on the aryl group is bromine, chlorine or fluorine,
R''' is alkyl, alkenyl or aryl of 1 to 15carbon atoms and substituted aryl forms where the substituent is fluorine, chlorine, bromine, nitro, cyano, hydroxyl, alkyloxy or mixtures of such substituents and Z is CO or CS.

2. Ethyl [3-(1-diphenoxyphosphinylbutyl)ureido]acetate.

3. Diphenyl [4-nitro-α-(ureido)benzyl]phosphonate.

4. Diphenyl [2-(3-phenylureido)ethyl]phosphonate.

5. Diphenyl [4-fluoro-α-(3-phenylureido)benzyl]phosphonate.

6. Diphenyl α-[3-(4-chlorophenyl)ureido]-4-hydroxy-3-methoxybenzylphosphonate.

7. Diphenyl α-(3,3-diphenylureido)-4-nitrobenzylphosphonate.

* * * * *

UNITED STATES PATENT OFFICE
CERTIFICATE OF CORRECTION

Patent No. 4,036,913  Dated July 19, 1977

Inventor(s) Gail H. Birum

It is certified that error appears in the above-identified patent and that said Letters Patent are hereby corrected as shown below:

Column 8, line 60, "NR" should read -- NH --.

Claim 4 should appear as follows:

4. Diphenyl[1-(3-phenylureido)ethyl]phosphonate.

Signed and Sealed this

Twenty-fourth Day of January 1978

[SEAL]

Attest:

RUTH C. MASON
*Attesting Officer*

LUTRELLE F. PARKER
*Acting Commissioner of Patents and Trademarks*